(12) United States Patent
Knorig

(10) Patent No.: US 6,264,633 B1
(45) Date of Patent: *Jul. 24, 2001

(54) BALLOON CATHETER

(75) Inventor: Joachim-Michael Knorig, Berlin (DE)

(73) Assignee: Willy Rüsch AG, Kernen-Rommelshausen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/112,279

(22) Filed: Jul. 9, 1998

(30) Foreign Application Priority Data

Jul. 31, 1997 (DE) .............................. 197 32 965

(51) Int. Cl.⁷ ...................... A61M 29/00; A61M 25/00; A61B 19/00
(52) U.S. Cl. ................... 604/102.01; 604/96.01; 604/104; 604/103.08; 604/532; 128/898; 600/435
(58) Field of Search ............... 604/96, 97, 102–104, 604/174, 523, 532, 101, 163–4; 600/433–35; 128/898

(56) References Cited

U.S. PATENT DOCUMENTS

| | | | |
|---|---|---|---|
| 5,035,694 | * 7/1991 | Kasprzyk et al. | 606/27 |
| 5,111,832 | * 5/1992 | Saksena | 128/898 |
| 5,270,005 | * 12/1993 | Raible | 422/46 |
| 5,353,787 | * 10/1994 | Price | 128/200.26 |
| 5,395,331 | * 3/1995 | O'Neill et al. | 604/96 |
| 5,423,745 | 6/1995 | Todd . | |
| 5,458,573 | * 10/1995 | Summers | 604/101 |
| 5,458,574 | * 10/1995 | Machold et al. | 604/101 |
| 5,462,529 | * 10/1995 | Simpson et al. | 604/101 |
| 5,478,309 | * 12/1995 | Sweezer et al. | 604/4 |
| 5,484,411 | * 1/1996 | Inderbitzen et al. | 604/96 |
| 5,484,412 | * 1/1996 | Pierpont | 604/101 |
| 5,549,551 | * 8/1996 | Peacock, III et al. | 604/96 |
| 5,620,418 | 4/1997 | O'Neil . | |
| 5,653,690 | * 8/1997 | Booth et al. | 604/96 |
| 5,674,198 | * 10/1997 | Leone | 604/101 |
| 5,713,861 | * 2/1998 | Vanarthos | 604/96 |
| 5,800,375 | * 9/1998 | Sweezer et al. | 604/102 |
| 5,810,757 | * 9/1998 | Sweezer, Jr. et al. | 604/4 |

FOREIGN PATENT DOCUMENTS

| | | |
|---|---|---|
| 0204218 A1 | 12/1986 | (EP) . |
| 0218275 A1 | 4/1987 | (EP) . |
| 0490459 A1 | 6/1992 | (EP) . |

* cited by examiner

Primary Examiner—Angela D. Sykes
Assistant Examiner—Patricia Bianco
(74) Attorney, Agent, or Firm—Paul Vincent

(57) ABSTRACT

A balloon catheter for medical applications has a balloon 11 in a tip region facing the patient having a structured outer surface 12. The structured outer surface 12 is formed by wave troughs and wave crests which are not connected to each other. The structured outer surface 12 of a balloon 11 can cling to adjacent surfaces. The balloon catheter is introduced via a left-ventricular cardiotomy in the tip region and inserted into the aorta ascendens. The balloon 11 occludes the aorta ascendens. The balloon allows cardioplegia to be performed and relieves the heart through suctioning-off. Particular applications for the balloon catheter include by calcification of the aorta ascendens, for effecting LIMA/RIMA-anastomoses, and when effecting venovenostomies.

6 Claims, 2 Drawing Sheets

BALLOON CATHETER

BACKGROUND OF THE INVENTION

The invention concerns a balloon catheter for medical applications having an inflatable balloon disposed on the catheter shaft for fixing the balloon catheter within an organ cavity or for blocking the lumen of an organ cavity.

This type of catheter is known in the art for a plurality of applications in urology, the tracheal area, or the esophagus.

Conventional catheters are, e.g. during intubation, fixed in the trachea.

In addition, blocking catheters are known in the art of heart surgery which are inserted into the aortic arch through the groin. The positioning of this type of blocking catheter is difficult from a technical point of view, has associated complications, and is time consuming. In addition, it is not possible to relieve the immobilized heart during cardioplegia.

It is therefore the purpose of the invention to create a balloon catheter which guarantees a liquid-tight and position-stable occlusion of the aorta, which gently interacts with the occluded organ cavity in the vicinity of the blocking, which allows for a short and simplified implantation path, and which simultaneously facilitates relieving the heart and cardioplegia.

SUMMARY OF THE INVENTION

This purpose is achieved in accordance with the invention in that the balloon has a structured and/or rugged outer surface.

The balloon catheter in accordance with the invention has the substantial advantage that the balloon can be pressed in a non-slipping fashion onto the aorta vessel intima. The structured outer surface of the rubber-elastic balloon can better seat on the inner surfaces of the vessels with increased friction without injuring the vessel structure in the occluded region. The outer surface of the rubber-elastic balloon has mountains and valleys which adjust to irregularities in the inner wall of the vessel and which hold onto the irregularities or given vessel structures when the balloon is inflated so that a positioned and inflated balloon does not move even under pressure to guarantee a liquid-tight blocking of an organ cavity.

A visible structured and/or rugged outer surface of the balloon guarantees that the catheter used has a balloon properly selected for the application at hand. If, in addition, the balloon is made from latex the excellent material properties thereof, namely extremely high stretchability, and good elasticity, can be advantageously utilized for blocking of an organ cavity.

In an additional configuration of the invention, the structurized and/or rugged outer surface is effected by means of a solvent and/or a coagulation agent, e.g. toluene, which gives the balloon its irregular outer surface.

This procedure for manufacturing a balloon in accordance with the invention has the advantage that the latex balloon can be produced with a dipping procedure. Directly following dipping, the latex film having the desired balloon shape is submerged into a predetermined solution which irregularly structures and roughens the outer surface of the latex balloon without negatively influencing the elasticity of the latex material for its intended application. The structuring of the outer surface of the balloon can also be effected mechanically or mechanically and thermally. The outer surface structuring provided by an appropriate solvent has the additional advantage for production of the balloon in accordance with the invention that this method step is simple and not time consuming.

In a further configuration of the invention, the latex balloon has a base form which is adjusted to a first and to a second end region on the shaft section of a catheter.

This has the advantage that the fundamental size of the manufactured balloon can be kept small and suitable end sections of the balloon can, for example, be manufactured having a size which is smaller than that of a shaft section of a catheter to assure that these end regions conform, without folds, to the outer surface of a shaft section when introduced thereon and stick thereto and/or are attachable to the catheter shaft in a liquid-tight and pressure-tight manner using threads.

In an improved embodiment of the invention, the balloon catheter has a guiding lumen in the catheter shaft which is closed on the side facing the patient and which ends in a catheter tip which is preferentially thickened. The catheter is formed and disposed in a stable location at the tip region of the balloon catheter. In addition, the balloon catheter has a first catheter shaft jacket which terminates at the end of the balloon facing away from the patient and which has at least one first eye. The first eye connects to a first lumen and provides communication between this first lumen and the outside environment. In addition, a second catheter jacket is provided for on the balloon catheter which is disposed on the first catheter jacket and ends at a separation from the first eye, wherein the second catheter jacket has at least one second eye which connects the second lumen to the outside.

The configuration of the balloon catheter in accordance with the invention facilitates applications in substantially three areas which, in part, allow for new techniques in heart surgery. The balloon catheter having the structured surface balloon can be used for operations, 1. where calcification does not permit a transverse clamping of the aorta;
2. for LIMA/RIMA anastomosis using MIS procedures; and
3. for MIS venovenostomy between the coronary vessel and the aorta descendens.

The abbreviations "LIMA" and "RIMA" stand for the left arterial mammaria interna and the right arterial mammaria interna respectively (the new designations: arteria thoracica interna left or right).

A balloon catheter having the features in accordance with the invention can be utilized as a transventricular aorta blocking balloon having a cardioplegia channel and a vent channel for use in bypass surgery. The balloon catheter in accordance with the invention facilitates aorta occlusion and cardioplegia of an arterialsclerosis-inflicted aorta without clamping. An aorta clamping (prior art) can damage the aorta wall and cause washing of calcium particles into the brain with associated embolic failure.

With the increase in the number of patients having terminal arterial sclerosis and the increasing frequency of patients required renewed operation, the use of the balloon catheter in accordance with the invention simplifies heart surgery on the patient. The balloon catheter in accordance with the invention has a guide channel for use of a mandrin. The inflatable latex balloon having the roughened outer surface facilitates a reliable blocking of the aorta and, via a first lumen, cardioplegia solutions can flow between the balloon and the aorta valve into the aorta and the coronary vessels. The heart undergoing cardioplegia is relieved via a second lumen and the blood received by the second lumen is transported to a heart-lung-machine. The improved balloon catheter in accordance with the invention can be used for secure blocking of the aorta ascendens during bypass operations even if the aorta ascendens has very strong calcification in this region. Conventional transverse clamping of the aorta could lead to aorta damage. The balloon catheter improved in accordance with the invention can also, however, be utilized in operations within the framework of the conventional minimal invasive coronary surgery as well as within the framework of minimally invasive coronary surgery under very new technology which also facilitates vein bypass.

During bypass operations the calcification in the aorta ascendens causes substantial medical problems. Within the framework of an invasive operation, the aorta ascendens has to be clamped in a transverse fashion with the associated danger of damage to the calcified aorta. If damage or destruction to the vessel thereby occurs the resulting medical problems can only be handled with extreme difficulty and can only be overcome by means of a very time-consuming operation. In addition, the clamping-off of the aorta ascendens can lead to the washing of calcium particles into the brain. This can lead clinically to a cerebral infarct with motoric and nerve failure in brain functions or to coma.

Up to this point in time, such complications have been avoided by carrying out the operation under deep hypothermic cautions. The patients are cooled down using the heart-lung-machine to a temperature of approximately 17° C. body-base-temperature. At this temperature, cell metabolism is reduced to a minimal degree. At this point in time, the heart-lung-machine is stopped and circulation interrupted.

During this period of time, the peripheral coronary anastomoses are sutured. The period of time during which circulation is interrupted cannot exceed approximately 60 minutes. Subsequent thereto, circulation is resumed and the patient is warmed. Clearly, this procedure can lead to severe post-operative complications especially with elderly and severely ill patients. The brains of such patients can suffer severe consequences. The patients have transitional symptoms and a state of confusion which often require a long and complicated intensive medical treatment. Additional organ failures are possible. In addition to these medical consequences, there are also financial considerations since the cooling and the warming-up requires a very long operation time. The extensive post-operative care and the necessary medication is extremely expensive. These above mentioned problems can be avoided with the improved balloon catheter in accordance with the invention to facilitate a new, alternative approach to bypass surgery.

In a preferred embodiment of the balloon catheter in accordance with the invention, a visible scale is disposed along the catheter shaft or introduced into the catheter material. This has the advantage that the operating physician can read-off the insertion depth of the balloon in the heart from the catheter shaft.

In addition to the device for simplified bypass surgery in accordance with the invention, a method for use of the balloon catheter is proposed with which the balloon catheter is introduced externally via a ventriculomy into the heart of a patient connected to a heart-lung-machine via the tip of the left ventricle. The tip, the balloon and the first eye of the balloon catheter are displaced through the aorta valve into the aorta ascendens and the second eye remains in the ventricle. The balloon catheter is properly positioned and inflated until the aorta ascendens is completely occluded. A cardioplegia solution is then infused via the first lumen and through the first eye out of the balloon catheter. Blood is suctioned into the heart-lung-machine via the second eye and the second lumen. With the prescribed function of the balloon catheter, coronary anostomies are effected and the balloon-induced occlusion is then terminated. Central anastomoses are subsequently effected and the balloon catheter is then finally removed from the heart.

As is known in the art, the operation begins with a mediane sternotomie. If, due to massive aorta sclerosis, a normal canalization of the aorta ascendens is not possible, these patients are arterially cannulised femorally through the groin. If a non-calcified region is present in the aorta ascendens it is then possible for the aorta ascendens to be arterially cannulised. The veinal connection to the heart-lung-machine then follows using conventional techniques. After the heart-lung-machine has full flow and the heart is relieved, a purse-string suture is applied at the tip of the left ventricle. The balloon catheter in accordance with the invention is then positioned from the outside into the heart and the penetration depth of the balloon catheter is marked using the scale introduced on the catheter. A small incision is then made in the purse-string suture and the balloon catheter in accordance with the invention is inserted into the left ventricle. Under further careful insertion, the catheter is guided through the aorta valve into the aorta ascendens until the marking on the balloon catheter agrees with the predetermined measured length. When the balloon catheter is properly placed, it is inflated until the aorta ascendens is completely occluded. Complete aorta closure is monitored by an echo cardiogram. Cardioplegia solution is infused via the first lumen (cardioplegia channel). The left ventricle is relieved via the second lumen (vent channel) and blood is suctioned into the heart-lung-machine. The coronary anastomosis is then effected in the usual fashion. After the anastomoses have been effected, the blocking of the aorta ascendens is terminated. The heart begins to beat. The central anastomoses are then fashioned. This can be done e.g. in the form of a connection to the truncus brachiocephalicus or to a non-calcified region of the aorta ascendens. A simple anastomosis is thereby sufficient with additional veins being implanted in the anastomosis-treated vein. The catheter is then removed and the purse-string suture released. This location is secured with a patch suture and the operation is ended. The heart should be locally cooled during the operation by external ice water rinsing.

Use of the improved balloon catheter in accordance with the invention in previously conventional minimal invasive coronary surgery has the advantage that the balloon catheter in accordance with the invention can be easily introduced into the heart via the tip of the heart by means of a minimally invasive and anterolateral thoracotomy. The aorta can be blocked (this was not possible in previous minimally invasive coronary surgery). Cardioplegia can be effected using the improved balloon catheter in accordance with the invention to thereby effect a secure high quality suturing of coronary anastomoses on non-beating, relieved hearts without bleeding from the coronary vessels. Previous minimally invasive methods sutured the anastomoses on the beating heart. Use of the catheter in accordance with the invention permits suturing of the anastomoses when the heart is stationary, as has been done up to this point in time in established operative procedures. The heart is relieved via the second lumen (vent channel). These measures prevent an excessive strain on the heart and facilitate luxation thereof.

To begin an MIS-operation (minimally invasive surgery), the heart-lung-machine is connected via the left or right side of the groin (arterial femoralis and veineral femoralis). The conventional MIS-left-sided mini-thoracotomy is then performed. Preparation of the arterial mammaria sinistra or dextra then follows. Following complete preparation, the end of the arterial mammaria is separated. A purse-string suture is applied to the tip of the heart. A small incision is made in the center of this purse-string suture and the improved balloon catheter in accordance with the invention is inserted via this incision through the ventricle via the aorta valve into the aorta. The aorta ascendens is then blocked by the balloon. The cardioplegia solution is infused into the root of the aorta via the first lumen of the balloon catheter (cardioplegia channel). After the heart has stopped beating, the left ventricle is relieved via the second lumen of the balloon catheter (vent channel). The coronary anastomosis can then be sutured on the immobilized heart. After the anastomoses have been constructed, the aorta blockage is removed. The heart begins to beat. The catheter is removed and the purse-string suture released. This position is then secured with a U-patch suture. The operation is concluded in the usual fashion.

Vein bypasses can also be performed using the improved balloon catheter in accordance with the invention by means of MIS-procedures. If the balloon catheter in accordance with the invention is positioned as described, additional vein bridges using V. Saphena Magna removed from the patient can be built between the coronary vessels and the breast wall arteries while the heart is relieved. After effecting the coronary anastomoses as described, the aorta, which is easily accessible through the lateral thoracotomy descendens, is tangentially clamped and holes are punched into the artery wall. The veins are sutured to the aorta wall and the tangential clamping is subsequently released. The operation is ended as already described.

Further advantages can be derived from the description of the accompanying drawing. The above mentioned features and those to be described further below in accordance with the invention can be utilized individually or collectively in arbitrary combination. The embodiments shown are not to be considered as exhaustive enumeration, rather have exemplary character only.

The invention is shown in the drawing and is further described with reference to embodiments.

DESCRIPTION OF THE PREFERRED EMBODIMENT

Figure 1:
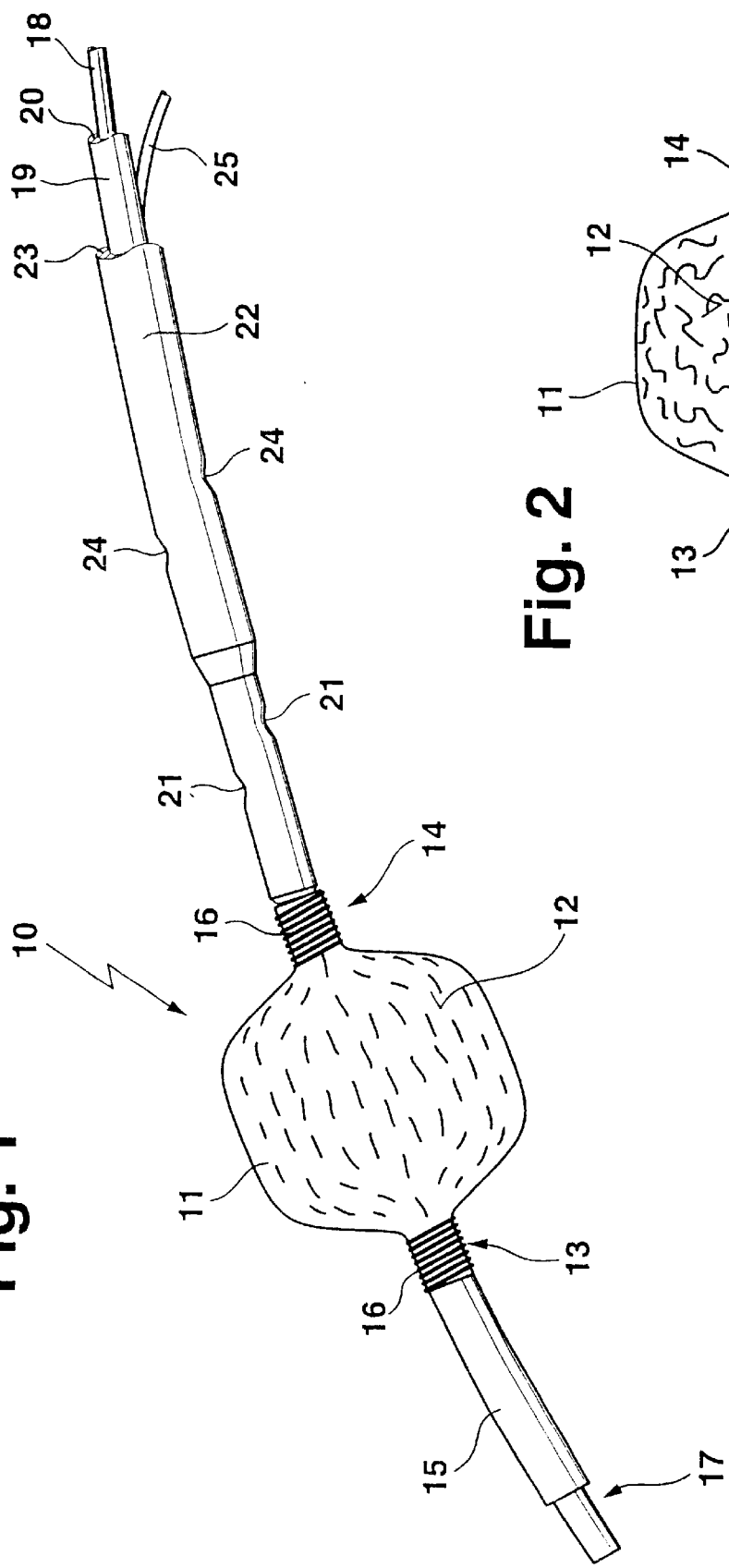
FIG. 1 shows a section of a balloon catheter in accordance with the invention in its tip region.

The individual figures of the drawing show the object of the invention in a partially highly schematic fashion and are not to be taken to scale. Some of the separate features shown in the individual drawings are strongly enlarged so that their construction can be more easily seen.

FIG. 1 shows a section of a balloon catheter 10 having a balloon 11, in its tip region, having a structured outer surface 12. The structured outer surface 12 is formed by mountains and valleys which prevent passage between adjacent valleys along the axial extent of the balloon 11. The rubber-elastic balloon 11 is preferentially made from latex and has a stable basic shape as well as a first end region 13 of stable shape and a second end region 14 of stable shape. The sizes of the end regions 13, 14 are adapted to a catheter shaft 15 onto which the balloon 11 is pulled. The balloon is glued to the catheter shaft 15 at a particular position and is also secured thereto using threads 16.

Various tips can be mounted to the catheter tip 17 in a permanent manner as required by the particular application.

The balloon catheter 10 has a guide lumen 18 via which a guide wire can be introduced into the balloon catheter 10. The guide wire can be used to additionally stiffen or deflect the catheter shaft 15.

The catheter shaft 15 has a first catheter jacket 19 defining a first lumen 20 at the side of the balloon 11 facing away from the patient. The first lumen 20 is connected to a first eye 21. The first lumen 20 is connected to the outside via the first eye 21. A second catheter jacket 22 is disposed over the first catheter jacket 19 and defines a second lumen 23 which is connected to the second eye 24. The second lumen 23 is connected to the surrounding environment via second eye 24. The balloon 11 can be inflated with a fluid, e.g. sodium chloride solution, via a balloon channel 25. The liquid located in the balloon 11 can likewise be drained via balloon channel 25.

Figure 2:
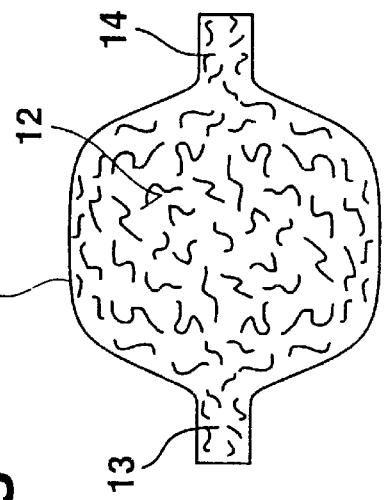
FIG. 2 shows an isolated balloon in accordance with the invention as it is disposed on a balloon catheter.

FIG. 2 shows the balloon 11 of FIG. 1. The latex-balloon 11 is produced by dipping an appropriate mould into liquid latex. The latex film located on the mould is then dipped into a solution, e.g. toluene, to impart a structurized rough outer surface to the vulcanized latex balloon 11 which adheres in a gentle but liquid-tight fashion in the blocking state to the inner wall of the vessel. The balloon 11 has, in addition to the structurized outer surface 12, a stable shape and shaped end regions 13, 14. The catheter shaft is inserted through the end regions 13, 14 up to a position at which it is glued or bound to the balloon 11.

Figure 3:
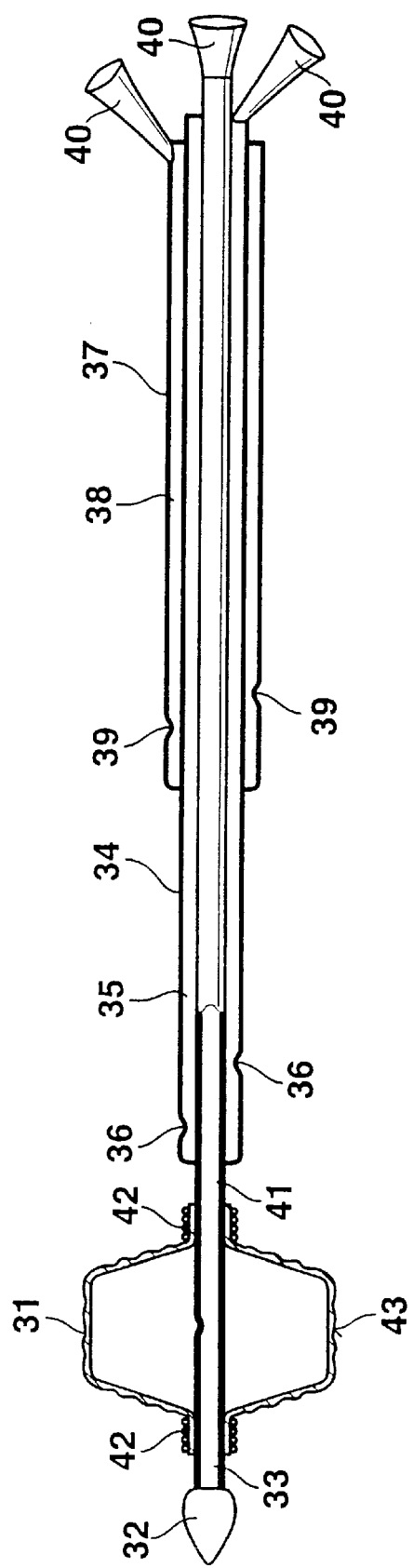
FIG. 3 is a balloon catheter in accordance with the invention for use in bypass surgery having a transventricular balloon for blocking the aorta, a first lumen (cardioplegia channel), and a second lumen (vent channel).

FIG. 3 shows an additional embodiment of a balloon catheter 30 having a balloon 31 and a tip 32. The balloon catheter 30 is shown substantially in cross-sectional view so that the lumina formed in the balloon catheter 30 can be seen.

A guide lumen 33 extends through the entire axial length of the balloon catheter 30 and is closed at the tip 32. A mandrin can be guided into guide lumen 33 to stiffen and/or to direct the balloon catheter 30. A first catheter jacket 34 defines a first lumen 35, which has a first eye 36 in an end region thereof. A second catheter jacket 37 defines a second lumen 38 which has a second eye 39 in an end region thereof. Conventional connecting members 40 are provided on the end of the balloon catheter 30 facing away from the patient to connect the described lumina to additional conduits. Both the tip 32, the balloon 31 and the first catheter jacket 34 are introduced on the catheter shaft 41. The second catheter jacket 37 is formed along a certain axial length on the first catheter jacket 34. The balloon 31 is glued to the catheter shaft 41 and also securely fixed on the catheter shaft 41 by means of a thread 42. The balloon 31 has a structured outer surface 43 by means of which it can adapt and cling strongly to a neighboring surface.

A balloon catheter for medical applications has a balloon 11 in a tip region facing the patient with a structured outer surface 12. The structured outer surface 12 is formed by wave troughs and wave crests which are not connected to each other. The structured outer surface 12 of a balloon 11 can adapt and cling to adjacent surfaces. The balloon catheter is introduced via a left-ventricular cardiotomy in the tip region and inserted into the aorta ascendens. The balloon 11 occludes the aorta ascendens. The balloon allows cardioplegia to be carried out and relieves the heart through suctioning.

I claim:

1. A balloon catheter for transventricular blocking of an aorta lumen, the balloon catheter comprising:
   an inner shaft member defining a guide lumen which extends into a catheter tip formed on said inner shaft member;
   an inflatable balloon attached to said inner shaft member, said inflatable balloon having a distal end proximate said tip of said inner shaft and having a proximal end, said balloon also having a structured outer surface;
   a first catheter jacket surrounding said inner shaft member and defining a first lumen, said first catheter jacket having a distal end sealed to said inner shaft member at a proximal separation from said proximal end of said balloon, said first catheter jacket having a first eye connecting said first lumen to a surrounding environment;
   a second catheter jacket surrounding said first catheter jacket to define a second lumen, said second catheter jacket having a distal end sealed to said first catheter jacket at a proximal separation from said first eye, said second catheter jacket having a second eye connecting said second lumen to the surrounding environment, said second eye being separated from said first eye by a distance between an aorta ascendens and a left ventricle, whereby said first eye is disposed in said aorta ascendens when said second eye is disposed in said left ventricle.

2. The balloon catheter of claim 1, wherein the balloon is made from latex.

3. The balloon catheter of claim 2, wherein said structured outer surface is formed through the action of one of a solvent and a coagulant to give said balloon an irregular outer surface.

4. The balloon catheter of claim 2, wherein said balloon has an intrinsically stable shape with first and second end regions thereof fitted over sections of said catheter shaft.

5. The balloon catheter of claim 1, wherein said outer surface is visually recognizable.

6. A method for using a balloon catheter, the balloon catheter for transventricular blocking of an aorta lumen, the balloon catheter having an inner shaft member defining a guide lumen which extends into a catheter tip formed on said inner shaft member, and with an inflatable balloon attached to said inner shaft member, said inflatable balloon having a distal end proximate said tip of said inner shaft and having a proximal end, said balloon also having a structured outer surface, and with a first catheter jacket surrounding said inner shaft member and defining a first lumen, said first catheter jacket having a distal end sealed to said inner shaft member at a proximal separation from said proximal end of said balloon, said first catheter jacket having a first eye connecting said first lumen to a surrounding environment, and with a second catheter jacket surrounding said first catheter jacket to define a second lumen, said second catheter jacket having a distal end sealed to said first catheter jacket at a proximal separation from said first eye, said second catheter jacket having a second eye connecting said second lumen to the surrounding environment, said second eye being separated from said first eye by a distance between an aorta ascendens and a left ventricle, the method comprising the steps of:
   a) introducing the balloon catheter from an outside via a ventriculotomy into a heart of a patient via a tip of said left ventricle;
   b) displacing said balloon and said first eye of said balloon catheter through an aorta valve into an aorta ascendens, said second eye remaining in said left ventricle, said first eye disposed between said balloon and said aorta valve;
   c) connecting said second lumen to a heart-lung machine;
   d) inflating said balloon to effect complete occlusion of the aorta after correct placement of the balloon catheter;
   e) infusing a cardioplegia solution via said first lumen to flow out of the balloon catheter via said first eye;
   f) suctioning blood into the heart-lung machine via said second eye and said second lumen;
   g) deflating said balloon to remove the occlusion caused thereby; and
   h) removing the balloon catheter from the heart.

* * * * *